United States Patent [19]

Reed et al.

[11] Patent Number: 5,396,002
[45] Date of Patent: Mar. 7, 1995

[54] PROCESS TO PRODUCE VINYLIDENE CHLORIDE USING PHASE TRANSFER CATALYST

[75] Inventors: Daniel J. Reed; T. Gayle Snedecor, Jr., both of Angleton, Tex.

[73] Assignee: The Dow Chemical Company, Midland, Mich.

[21] Appl. No.: 108,957

[22] Filed: Aug. 18, 1993

[51] Int. Cl.⁶ .............................................. C07C 17/34
[52] U.S. Cl. .................................. 570/228; 585/641; 585/642
[58] Field of Search .................. 570/228; 585/641, 642

[56] References Cited

U.S. PATENT DOCUMENTS 3,664,966  5/1972  Gordon ............................... 252/430
3,754,044  8/1973  Hargreaves, II et al. ...... 260/654 D
4,308,410  12/1981  Hall et al. ............................ 570/229
4,418,232  11/1983  Maurin, III ......................... 570/228
4,605,800  8/1986  Englert, Jr. et al. ............... 570/228

*Primary Examiner*—Howard T. Mars
*Attorney, Agent, or Firm*—Robert M. O'Keefe

[57] ABSTRACT

The invention concerns a process for producing unsaturated compounds from chlorinated alkanes by dehydrochlorination wherein a phase transfer catalyst is used during reaction of chlorinated alkane with aqueous base. After dehydrochlorination, the products are distilled or flashed off. Then, the phase transfer catalyst is recovered and reused by extracting the catalyst from spent aqueous base with fresh chlorinated alkane and using the mixture of chlorinated alkane and catalyst from the extraction as feedstock.

10 Claims, 1 Drawing Sheet

5,396,002

PROCESS TO PRODUCE VINYLIDENE CHLORIDE USING PHASE TRANSFER CATALYST

BACKGROUND OF INVENTION

This invention concerns the production of unsaturated compounds from chlorinated compounds using phase transfer catalysts in combination with a base.

Various methods are known to dehydrohalogenate halogenated hydrocarbons using a base and a phase transfer catalyst. For instance, U.S. Pat. No. 3,664,966 describes such a process wherein an aqueous base in conjunction with an organic quaternary salt. In the examples, 1,1-dichloroethylene (vinylidene chloride) is produced from 1,1,2-trichloroethane. The advantages of the phase transfer catalyst is an increase in reaction rate while allowing the reaction to be conducted at lower temperatures.

A similar process is described in U.S. Pat. No. 3,754,044. In this patent, a quaternary ammonium compound and a phosphate ester are utilized in combination as the phase transfer catalyst system. The phosphate ester is taught to act as a promoter.

While the processes described above produce enhanced reaction rates, such methods have generally not been used on a commercial scale because the phase transfer catalysts are expensive and lost during the process. Thus, such processes do not produce the desired products in a cost effective manner.

There followed U.S. Pat. No. 4,418,232 which describes an improved dehydrohalogenation process wherein a phase transfer catalyst is used. In this process, a cascade arrangement of reactors is described such that partially spent alkali solution from the first reactor is recycled back to a stage reactor prior to the primary reactor where fresh caustic solution is introduced. While this process recycles the caustic, the phase transfer catalyst is in large part not recycled because the phase transfer catalysts have greater solubility in the organic phase than in the aqueous phase.

More recently, U.S. Pat. No. 4,605,800 describes an improved dehydrohalogenation process to produce chloroprene from 3,4-dichlorobutene-1 using a phase transfer catalyst and caustic. In this process, the reactor effluent is sent to a decanter where the organic phase is separated from the aqueous phase. The organic phase is then sent to a steam-stripper whereby product is recovered and the heels from the stripper are returned to the reactor. However, since contaminants are present in the heels which would build-up if continuously recycled, from 2 to 20 percent of the heels are purged to prevent contaminant build-up. Moreover, it is know that phase transfer catalysts in general will decompose to some extent at temperatures greater than 130° C. When this is done, catalyst is also purged. In addition, catalyst is lost in the decanter as well as the steam-stripper. Hence, make up catalyst must be added to the heels to maintain the proper amount of catalyst in the reaction.

It is apparent that new and improved processes are desirable in dehydrohalogenation processes using phase transfer catalyst to provide more cost effective methods of production.

SUMMARY OF INVENTION

This invention, in one respect, is a process for producing unsaturated compounds which comprises:

(A) contacting a chlorinated alkane with an aqueous base solution in the presence of a phase transfer catalyst to form an unsaturated compound;

(B) distilling the unsaturated compound to make a bottoms mixture containing the residual of the aqueous basic solution and phase transfer catalyst;

(C) adding chlorinated alkane to the bottoms mixture from Step B and mixing the resulting admixture so that the phase transfer catalyst is extracted into the chlorinated alkane to form an organic solution of chlorinated alkane and phase transfer catalyst; and (D) using the organic solution from Step C as at least a portion of the chlorinated alkane and phase transfer catalyst employed in Step A.

In another respect, this invention is a process for producing vinylidene chloride which comprises:

(A) contacting 1,1,2-trichloroethane with an aqueous sodium hydroxide solution in the presence of a phase transfer catalyst to form vinylidene chloride at a temperature such that the vinylidene chloride is distilled off from the aqueous base solution and a spent aqueous base solution containing phase transfer catalyst is formed;

(B) adding 1,1,2-trichloroethane to the spent aqueous sodium hydroxide solution containing phase transfer catalyst and mixing the resulting admixture so that the phase transfer catalyst is extracted into the 1,1,2-trichloroethane to form an organic solution of 1,1,2-trichloroethane and phase transfer catalyst; and (C) using the organic solution from Step B as at least a portion of the 1,1,2-trichloroethane and phase transfer catalyst employed in Step A.

The processes of this invention recover and recycle a high percentage of phase transfer catalyst. Consequently, this invention provides commercially desirable methods of producing unsaturated compounds from chlorinated alkanes with efficient recovery and recycle of phase transfer catalyst.

DETAILED DESCRIPTION OF INVENTION

Figure 1:
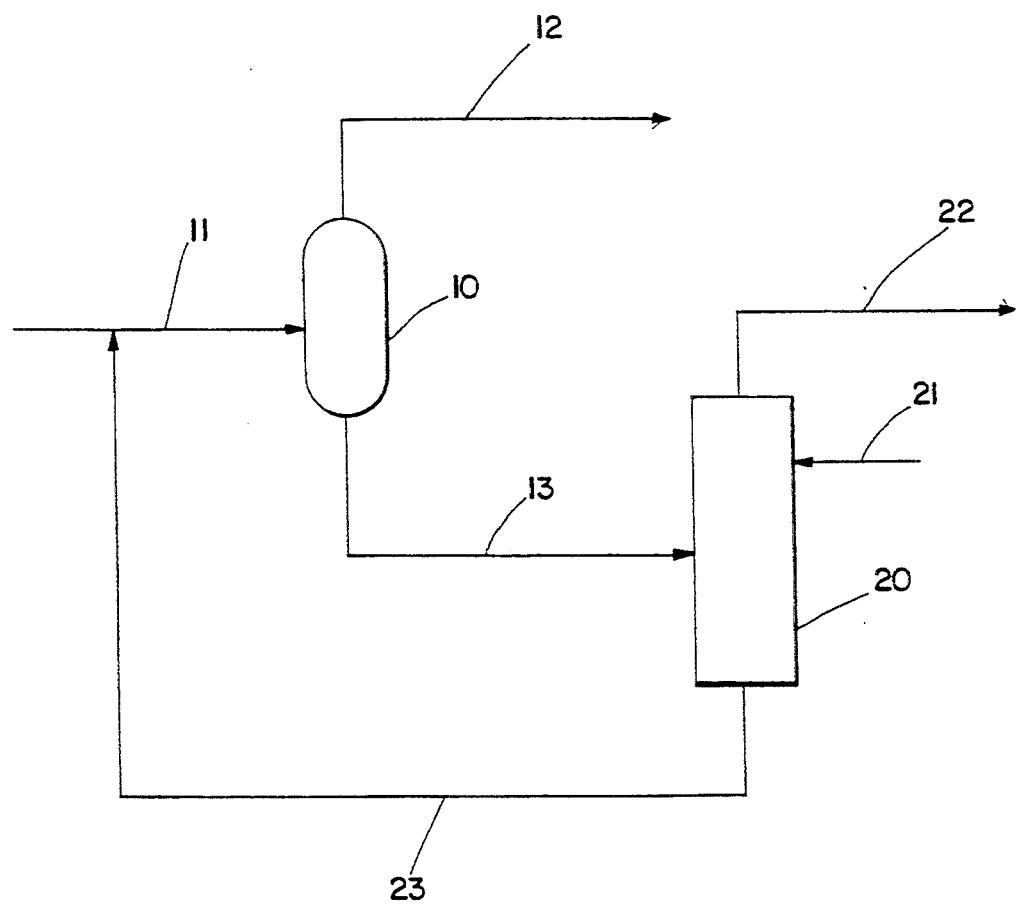
FIG. 1 is a schematic diagram of the present invention.

In the practice of this invention, the starting compounds to be dehydrochlorinated are any chlorinated alkanes which may be dehydrochlorinated in the process of this invention. Preferably, the starting compounds include chlorinated ethanes, propanes, and butanes that have at least one hydrogen. More preferably, the starting compounds are chlorinated ethanes that have at least one hydrogen. Preferred chlorinated ethanes are chloroethane, 1,1-dichloroethane, 1,2-dichloroethane, 1,1,1-trichloroethane, and 1,1,2-trichloroethane. The products of the process are unsaturated. Preferred products include vinyl chloride and 1,1-dichloroethene (vinylidene chloride).

The chlorinated alkane is contacted with an aqueous base solution. The aqueous base solution can be based on the hydroxides and carbonates of alkali and alkaline earth metals. Preferred aqueous base solutions are aqueous solutions of sodium or potassium hydroxides. The concentration of the aqueous solutions is not critical, but generally is 0.1N to 10N. Likewise, the amount of base is not critical, but a slight molar excess relative to the chlorinated ethane is generally used. Typically, the mole ratio of base to chlorinated solvent is 1:2 to 2:1.

The phase transfer catalysts which can be used in this invention include any compounds which catalyze the process of this invention to make unsaturated products from chlorinated alkanes. Classes of such phase transfer catalysts include quaternary ammonium salts, quaternary phosphonium salts, quaternary sulfonium salts, cyclic ethers (crown ethers), ether-alcohols, and betaines. Preferably, the phase transfer catalyst is a quaternary ammonium salt. The preferred quaternary ammonium salts are of the formula $R_4NX$ wherein R is independently in each occurrence is a $C_{1-20}$ alkyl, $C_{2-20}$ alkenyl, or $C_{7-20}$ aralkyl and wherein X is Cl, Br, I or F. X is preferably Cl. Generally, longer alkyl groups in the quaternary ammonium salts perform better in the process of this invention. Examples of preferred quaternary ammonium salts include benzyltrimethylammonium chloride, benzyltriethylammonium chloride, and benzyltributylammonium chloride with benzyltributylammonium chloride being most preferred in this group. The amount of the quaternary ammonium salts is 0.001 to 10 weight percent based on chlorinated ethane starting material with 0.1 to 0.5 weight percent being preferred.

The contacting of the reactants can occur at any temperature which will convert at least a portion of the chlorinated ethane to product. Generally, the temperature will be from 0° to 150° C. Pressure is sufficient to maintain substantially liquid conditions of reactants. The contacting typically occurs under strong agitation or circulation as practiced by those skilled in the art, such as by introducing the reactants in or near a pump. This strong circulation is employed to provide maximum contact of aqueous solution and organic starting material, the organic starting material being sparingly soluble in the aqueous solution.

The contacting can be carried out using conventional equipment designed for such purpose. The process can be run batch-wise or continuously.

After the contacting has proceeded to the desired level, the product is distilled off or flashes off during the process to leave the residual of the aqueous base solution which contains phase transfer catalyst. The residual leaves the reactor. The distillation temperature will vary depending on the chlorinated alkane and reaction products. Reduced pressure can be used to hasten distillation. The distillation can be performed using conventional equipment and techniques. In addition, the products can be further purified by well known methods such as additional distillation steps.

The bottoms from the distillation next go to a liquid/liquid extractor wherein fresh chlorinated alkane is added. During the extraction, the volume ratio of aqueous to organic phase can vary widely, but generally is from about 10:1 to about 1:10 based on weight, preferably 1:2 to 2:1. After addition of the chlorinated alkane, the entire mixture is mixed so that the aqueous and organic phases make intimate contact so that a substantial portion of the phase transfer catalyst is extracted into the organic phase. Preferably, greater than 95 percent of the phase transfer catalyst is extracted into the organic phase. The phases are then allowed to separate and the organic phase is recovered with the aqueous phase being disposed of or steam stripped to recover the saturated organics.

The organic phase, which comprises chlorinated alkane and phase transfer catalyst, is next recycled back to the primary reactor wherein the contacting occurs. Due to the slight loss of phase transfer catalyst, an appropriate amount of phase transfer catalyst can be added when desired to the primary reactor. Higher ratios of organic phase to aqueous phase will generally enable a greater amount of phase transfer catalyst being extracted. In the extraction, the temperature can be from 0° to 150° C., preferably from 20° C. to 100° C. Higher temperatures tend to decompose the phase transfer catalysts. Pressures can be up to about 300 psig during the extraction. The amount of time needed for the extraction can vary depending on the conditions, but generally is from 1 minute to 4 hours. Additional extraction stages can be utilized to further increase recovery of phase transfer catalyst.

The process of this invention can be understood by referring to FIG. 1.

Aqueous sodium hydroxide, 1,1,2-trichloroethane, and benzyltributylammonium chloride (BTBAC) are introduced into reactor 10 through line 11. In reactor 10 the 1,1,2-trichloroethane is dehydrochlorinated to form 1,1-dichloroethene (vinylidene chloride) which flashes off and exists reactor 10 through line 12. The spent aqueous sodium hydroxide solution which contains BTBAC exits reactor 10 through line 13 and enters liquid/liquid extractor 20. Fresh 1,1,2-trichloroethane enters liquid/liquid extractor 20 through line 21. In liquid/liquid extractor 20 the fresh 1,1,2-trichloroethane and spent aqueous sodium hydroxide solution are circulated to extract the BTBAC into the 1,1,2-trichloroethane. The extracted spent sodium hydroxide solution exits liquid/liquid extractor 20 through line 22. 1,1,2-trichloroethane which contains BTBAC exits liquid/liquid extractor 20 though line 23 and is then introduced into line 11 wherein sufficient make up BTBAC is added along with fresh aqueous sodium hydroxide and any needed 1,1,2-trichloroethane. While FIG. 1 shows a single liquid/liquid extractor, additional liquid/liquid extractors can be employed to increase phase transfer catalyst recovery.

The invention is now illustrated by the following example which should not to be construed to limit the scope of the invention or claims.

EXAMPLE 1

An aqueous sodium hydroxide solution was prepared that had a composition similar to that of spent solution from a commercial process used to make vinylidene chloride. The aqueous sodium hydroxide solution contained 0.3 weight percent NaOH and 21 NaCl to which was added 5,000 ppm of benzyltributylammonium chloride (BTBAC). Portions of the spent aqueous sodium hydroxide solution were contacted with fresh 1,1,2-trichloroethane in weight ratios denoted below in Table 2 (as "O/A", meaning organic to aqueous ratio). The mixture of organic and aqueous phases were thoroughly mixed and then the amount of BTBAC in the organic layer determined by gas chromatography. The results are reported below in Table 1.

TABLE 1

| O/A w/p | % BTBAC Recovered |
|---------|-------------------|
| 1:1     | 98.6              |
| 1:2     | 97.5              |
| 1:3     | 93.4              |

The mixture of 1,1,2-trichloroethane and BTBAC could be recycled back to a primary reactor in a process to make vinylidene chloride wherein aqueous sodium hydroxide is contacted with 1,1,2-trichloroethane in the presence of a quaternary ammonium salt such as BTBAC.

What is claimed is:

1. A process for producing unsaturated compounds which comprises:
   (A) contacting a chlorinated alkane with an aqueous base solution in the presence of a phase transfer catalyst to form an unsaturated compound;
   (B) distilling the unsaturated compound to make a bottoms mixture containing the residual of the aqueous basic solution and phase transfer catalyst;
   (C) adding chlorinated alkane to the bottoms mixture from Step B and mixing the resulting admixture so that the phase transfer catalyst is extracted into the chlorinated alkane to form an organic solution of chlorinated alkane and phase transfer catalyst; and
   (D) using the organic solution from Step C as at least a portion of the chlorinated alkane and phase transfer catalyst employed in Step A.

2. The process of claim 1 wherein the chlorinated alkane is a chlorinated ethane, propane, or butane containing at least one hydrogen.

3. The process of claim 1 wherein the phase transfer catalyst is a quaternary ammonium salt of the formula $R_4NX$ wherein R is independently in each occurrence is a $C_{1-20}$ alkyl, $C_{2-20}$ alkenyl, or $C_{7-20}$ aralkyl and wherein X is Cl, Br, I or F.

4. The process of claim 1 wherein the phase transfer catalyst is benzyltrimethylammonium chloride, benzyltriethylammonium chloride, or benzyltributylammonium chloride.

5. The process of claim 1 wherein the aqueous base solution is aqueous sodium hydroxide.

6. The process of claim 1 wherein the chlorinated alkane is chloroethane, 1,1-dichloroethane, 1,2-dichloroethane, 1,1,1-trichloroethane, or 1,1,2-trichloroethane.

7. A process for producing vinylidene chloride which comprises:
   (A) contacting 1,1,2-trichloroethane with an aqueous sodium hydroxide solution in the presence of a phase transfer catalyst to form vinylidene chloride at a temperature such that the vinylidene chloride is distilled off from the aqueous base solution and a spent aqueous base solution containing phase transfer catalyst is formed;
   (B) adding 1,1,2-trichloroethane to the spent aqueous sodium hydroxide solution containing phase transfer catalyst and mixing the resulting admixture so that the phase transfer catalyst is extracted into the 1,1,2-trichloroethane to form an organic solution of 1,1,2-trichloroethane and phase transfer catalyst; and
   (C) using the organic solution from Step B as at least a portion of the 1,1,2-trichloroethane and phase transfer catalyst employed in Step A.

8. The process of claim 7 wherein the phase transfer catalyst is a quaternary ammonium salt of the formula $R_4NX$ wherein R is independently in each occurrence is a $C_{1-20}$ alkyl, $C_{2-20}$ alkenyl, or $C_{7-20}$ aralkyl and wherein X is Cl, Br, I or F.

9. The process of claim 8 wherein X is Cl.

10. The process of claim 7 wherein phase transfer catalyst is benzyltrimethylammonium chloride, benzyltriethylammonium chloride, or benzyltributylammonium chloride.

* * * * *